United States Patent [19]

Coin

[11] Patent Number: 5,458,111
[45] Date of Patent: Oct. 17, 1995

[54] COMPUTED TOMOGRAPHIC COLONOSCOPY

[75] Inventor: Carl G. Coin, Long Key, Fla.

[73] Assignees: William C. Bond; Thomas P. Stafford; both of Islamorada, Fla.

[21] Appl. No.: 300,943

[22] Filed: Sep. 6, 1994

[51] Int. Cl.$^6$ ........................................................ A61B 5/00
[52] U.S. Cl. ........................................ 128/747; 128/653.1
[58] Field of Search ............................. 128/653.1, 653.2, 128/653.4, 654, 660.07, 660.08, 747

[56] References Cited

U.S. PATENT DOCUMENTS

| | | | |
|---|---|---|---|
| 4,243,652 | 1/1981 | Francis | 128/654 |
| 4,391,280 | 7/1983 | Miller | 128/654 |
| 4,874,362 | 10/1989 | Wiest et al. | 128/747 |
| 4,993,415 | 2/1991 | Long | 128/653.4 |
| 5,006,109 | 4/1991 | Dougles et al. | 128/747 |
| 5,023,072 | 6/1991 | Cheng | 128/653.4 |
| 5,322,070 | 6/1994 | Goodman et al. | 128/747 |

*Primary Examiner*—Max Hindenburg
*Attorney, Agent, or Firm*—Malloy & Malloy

[57] ABSTRACT

A generally non-invasive method of colon examination in which the patient's colon is first inflated with gas, and then a plurality of cross-sectional images of the colon are taken by CT scanning along the longitudinal axis of the abdomen. Sets of data corresponding to each cross-sectional image are stored in computer memory. These sets of data are processed by a first computer program that reconstructs a three-dimensional model of the entire colon. Data corresponding to the reconstructed three-dimensional model of the colon are also stored in computer memory. A second computer program processes the original sets of data and the three-dimensional model data to reconstruct, for successive thin segments along the length of the entire colon, a cross-sectional image for each segment which is perpendicular to the longitudinal axis of the colon lumen. These reconstructed images, which provide an exact simulation of the interior of the colon that would be viewed by means of colonoscopy, can be retrieved from memory and displayed for examination on a conventional video monitor, enabling the physician to detect any abnormalities of the colon wall anatomy which would tend to indicate the presence of an abnormality such as a polyp or tumor.

12 Claims, 2 Drawing Sheets

COMPUTED TOMOGRAPHIC COLONOSCOPY

BACKGROUND OF THE INVENTION

1. Field of the Invention

The present invention relates to a safe and effective method for examining a colon which is generally non-invasive, substantially rapid, and which provides a continuous unobstructed view of the internal surface of the colon wall that facilitates detection and diagnosis of abnormalities in the colon anatomy.

2. Description of the Related Art

There are presently two conventional methods utilized most often for examining the colon to detect abnormalities such as tumors or inflammatory processes in the anatomy of the colon. One standard procedure is the colonoscopy, which consists of a direct endoscopic examination of the colon with a flexible tubular structure known as a colonoscope which has fiber optic capabilities at one end thereof. The colonoscope is inserted through the patient's anus and directed along the length of the colon, thereby permitting direct endoscopic visualization of the colon polyps and tumors and in some cases, providing a capability for endoscopic biopsy and polyp removal. Although it does provide a precise means of colon examination, colonoscopy is time-consuming, expensive to perform, and requires great care and skill by the examiner, thorough patient preparation including purgatives and enemas, and usually a moderate anesthesia. Moreover, since colonoscopy is an extremely invasive procedure, there is a significant risk of injury to the colon and the possibility of colon perforation and peritonitis, which can be fatal.

Another standard procedure for examining the colon involves a "barium enema" followed by a fluoroscopic and radiographic examination. In this procedure, a solution of barium sulfite alone or mixed with air is first injected into the patient's colon by means of an enema, and then a fluoroscopic and radiographic examination of the colon is performed. This examination requires detailed observation by a radiologist, who must palpate the patient's abdomen and repeatedly reposition the patient for the taking of a first set of x-rays. After these initial x-rays are completed, the patient evacuates the barium mixture and additional x-rays are taken. The total examination procedure can be of considerable duration, lasting from 20 minutes to 1½ hours, and is very uncomfortable and demanding both for the patient as well as the radiologist and x-ray technician. During the examination, the patient may experience numerous difficulties such as problems retaining the barium mixture, pain associated with palpation, and colon spasms. It is also possible for the colon to become impacted with barium, leading to severe constipation and interference with later diagnostics, thereby requiring the barium to be fully purged using powerful and sometimes dangerous laxatives. This purging of the barium may also in rare instances result in colon perforation with barium peritonitis, which is a lifetime debilitating and potentially fatal complication, Because of the significant difficulties and potential complications involved with both of the conventional procedures for examining the colon, there is still a need for a method of examining a patient's colon which provides a precise and accurate visualization of the colon anatomy to detect abnormalities, is easy to conduct by medical personnel and generally non-invasive compared with conventional procedures, and which involves minimal discomfort to the patient.

Summary of the Invention

The present invention is directed towards a generally non-invasive method of colon examination in which the patient's colon is first inflated with gas, and then a plurality of cross-sectional images of the colon are taken preferably by CT scanning along the longitudinal axis of the abdomen. A set of projection data obtained from the scanning and corresponding to each cross-sectional image is stored in computer memory. These sets of data are processed by a first computer program that reconstructs a three-dimensional model of the entire colon. Data corresponding to the reconstructed three-dimensional model of the colon are also stored in computer memory. A second computer program processes the original sets of data and the three-dimensional model data to reconstruct, for successive thin segments along the length of the entire colon, a cross-sectional image for each segment which is perpendicular to the longitudinal axis of the colon lumen. These reconstructed cross-sectional images, which provide an exact simulation of the interior of the colon that would be viewed by means of colonoscopy, can be displayed on a video monitor and examined to detect any abnormalities of the colon wall anatomy which would tend to indicate the presence of a tumor or inflammation.

It is an object of the present invention to provide an extremely accurate, relatively non-invasive method of examining a colon in an uncollapsed state whereby cross-sectional images of sections of the colon which are perpendicular to the longitudinal axis of the colon lumen can be viewed.

Another object of the present invention is to provide a method of examining a colon which minimizes the significant discomfort usually experienced by the patient during a conventional colon examination procedure.

A further object is to provide a method of examining a colon which is generally non-invasive so as to minimize any health risks associated with the examination procedure.

Still another object of the present invention is to provide a method of examining a colon which requires minimal patient preparation, can be completed in a substantially rapid period of time, and is relatively inexpensive to perform.

Yet another object of the present invention is to provide a method of examining a colon which will promote frequent examination and early detection of conditions affecting the colon.

BRIEF DESCRIPTION OF THE DRAWINGS

The invention will be better understood after reading the following detailed description of the presently preferred embodiment thereof with reference to the appended drawings in which.

Detailed Description of the Preferred Embodiment

Figure 1:
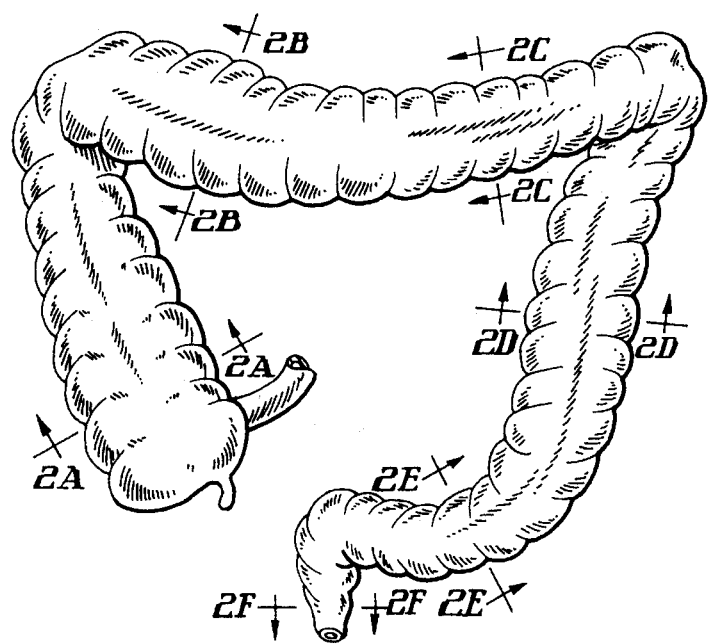
FIG. 1 is a front perspective view of a colon.
Figure 2A:
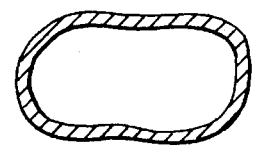
FIGS. 2A through 2F illustrate a plurality of cross-sectional images produced by the method of the present invention for the like-numbered segments indicated in FIG. 1.
Figure 2B:
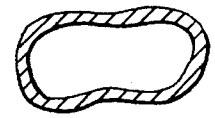
Figure 2C:
Figure 2D:
Figure 2E:
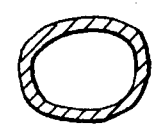
Figure 2F:

The method of the present invention requires initially that the patient's colon be filled with a gaseous contrast agent, which preferably can be ambient air, carbon dioxide, xenon or nitrous oxide. If xenon or nitrous oxide is selected, a topical anesthetic effect will be produced. The gas is injected into the colon by means of a pump having an enema tip that is inserted into the patient's rectum. The purpose of inflating the colon is two-fold. First, the colon normally sits within the abdomen in a collapsed configuration, which does not permit accurate viewing of its true internal structure. After being filled with gas, as shown in FIG. 1, the colon assumes a defined shape which facilitates examination of its internal wall surfaces. Second, the gas acts as a contrast agent that is extremely distinguishable from structures such as water, fat and tissue surrounding the gas. It will be understood by those skilled in the art that the x-ray absorption values for gas, as designated in Hounsfield Units ("H.U.") along the Hounsfield Scale of x-ray absorption values, are at the extreme low end of the scale at approximately −1000 H.U., compared to fat in the colon wall which has a value of about −100 H.U., water which has a value of 0, and bone, which is very dense and has a value of 1000 H.U. Gas therefore acts as an effective contrast agent when utilized in conjunction with transmission imaging of a body as by computed tomographic ("CT") scanning.

After the patient's colon has been inflated, multiple cross-sectional images of the entire colon are taken along the longitudinal axis of the patient's abdomen, preferably by CT scan employing helical scan imaging. Alternatively, a magnetic resonance imaging apparatus may be utilized to obtain the cross-sectional images. This CT scanning produces sets of projection data corresponding to standard cross-sectional images of the colon taken generally along the longitudinal axis of the abdomen, with the sets of data being transmitted to computer memory for storage therein. Representative illustrations of such cross-sectional images are shown in FIGS. 5A–5F. It is known in the art to process these sets of projection data by computer to produce the cross-sectional images shown in these Figures and labelled as prior art, and to display such cross-sectional images on a conventional video monitor or to photograph the image by means of a computer controlled camera. It will be appreciated, however, that although the prior art cross-sectional images that can be obtained from the CT scanning are of extremely high resolution, diagnosis of abnormalities in the colon anatomy from an examination of such images may be hampered by the obliquity of projections resulting from the complex curvature of the colon within the abdomen.

After the CT scanning is completed, a first computer program processes the sets of projection data to reconstruct a three-dimensional model of the colon, as shown in FIG. 1. Preferably, this reconstructed three-dimensional model will be a model of the gas-filled lumen of the colon. This first reconstruction program requires that an initial, representative prior art cross-sectional image of the colon obtained by the CT scanning be displayed on a display means such as a high resolution video monitor. Next, a cursor is positioned on the lumen of the displayed prior art cross-sectional image through the use of input means such as a mouse or keyboard. In the preferred embodiment, the cursor comprises a small circle having a diameter preferably in the range of 5–20 millimeters. This outlined circle on the lumen of the displayed prior art cross-sectional image provides the starting point for this first program, which operates to join together sections that are contiguous with the displayed prior art cross-sectional image and which are in the same range of x-ray absorption values as gas, to form a three-dimensional model of the colon. In the preferred embodiment, the three-dimensional model will actually be a model of the gas-filled lumen of the colon. Following the execution of this first reconstruction program, data representing the reconstructed three-dimensional colon model are also stored in computer memory.

After the three-dimensional model of the colon has been reconstructed, a second computer program processes the initial sets of data and the three-dimensional model data to reconstruct, for successive thin segments along the length of the entire colon, cross-sectional images which provide a precise simulation of images of the interior of the colon along its length similar to that which would be viewed by colonoscopy. This second program functions by selecting contiguous thin colon segments along the length of the entire colon and reconstructing for each segment the one cross-sectional view thereof which is perpendicular to the longitudinal axis of the colon lumen. In the preferred embodiment, the thickness of these segments will be selectively variable by the user and preferably will be in the range of 1–10 millimeters. In operation, this second program evaluates and processes the data stored in computer memory using the parameters of smallest cross-sectional diameter, area and circumference as applied to each segment to reconstruct the one desired cross-sectional image for that segment which is perpendicular to the longitudinal axis of the colon lumen. Data representing each of the desired cross-sectional images is then stored in computer memory, for subsequent retrieval and viewing of the images. The program also preferably includes the capability to reconstruct the tissue surrounding the periphery of the lumen of each cross-sectional image, at a tissue thickness that can be selectively varied by the user. In a preferred embodiment, the resultant reconstructed images produced by the second program, examples of which are shown in FIGS. 2A through 2F and which correspond to like-numbered segments in FIG. 1, will enable a visualization of both the internal and the external wall surfaces for each cross-sectional image.

Figure 4:
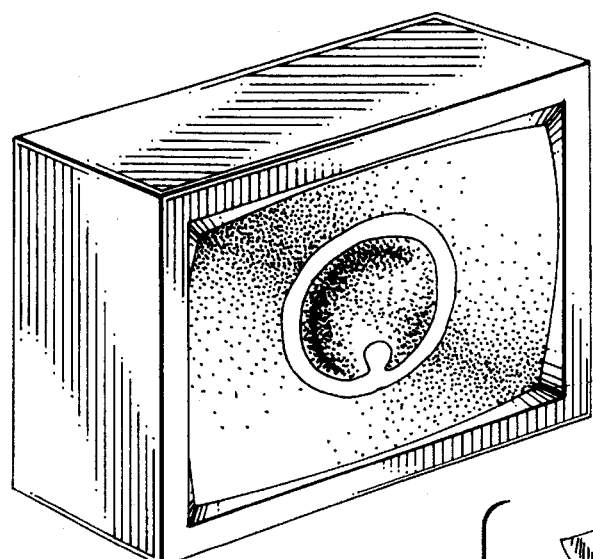
FIG. 4 is a view taken along lines 4—4 of FIG. 3 of a cross-sectional image produced by the method of the present invention for the colon segment adjacent the cursor in FIG. 3.
Figure 3:
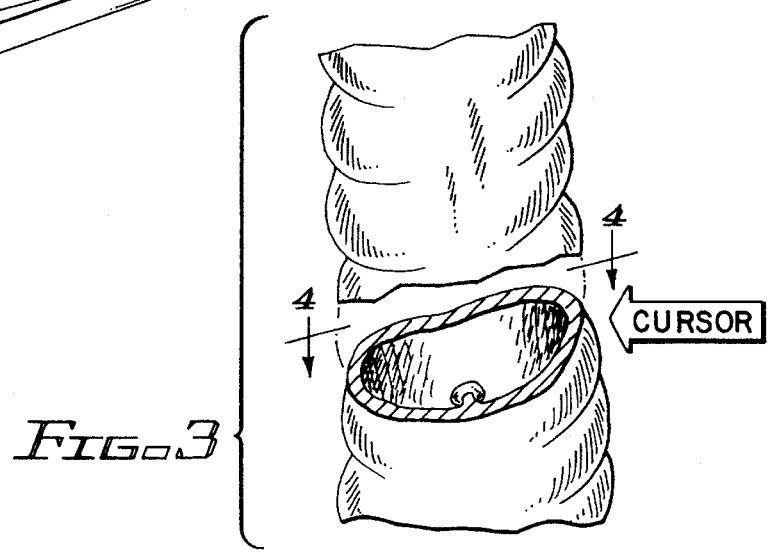
FIG. 3 shows an exploded view of a portion of the colon with a cursor positioned adjacent a selected colon segment depicted in cut-away to show the presence of a polyp.
Figure 5:
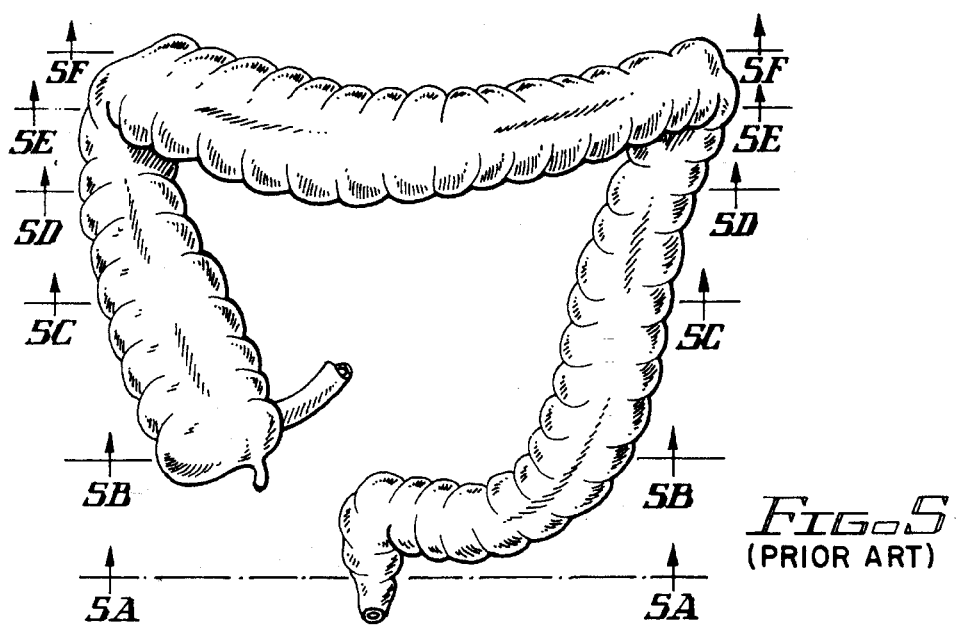
FIGS. 5 and 5A–5F illustrate standard prior art cross-sectional images of the colon produced by CT scanning.
Figure 5A:
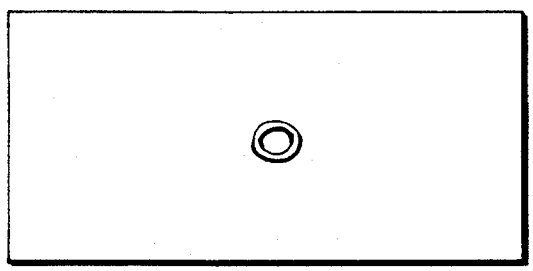
Figure 5D:
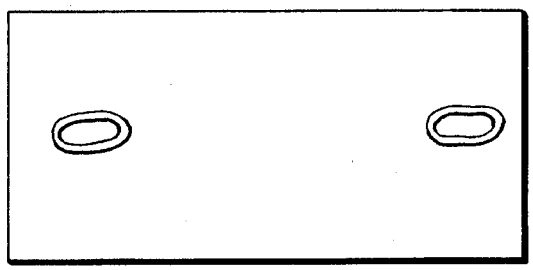
Figure 5B:
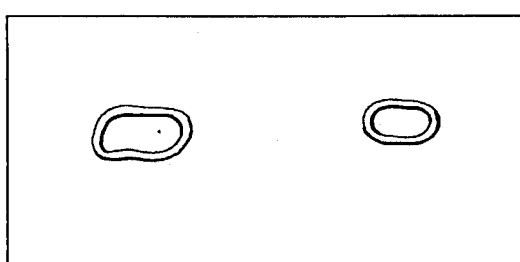
Figure 5E:
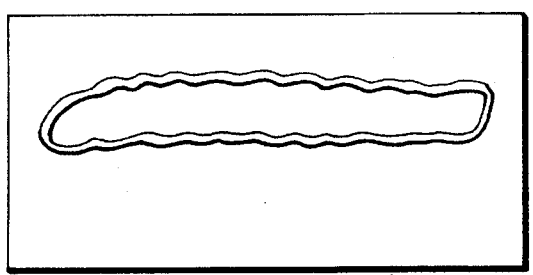
Figure 5C:
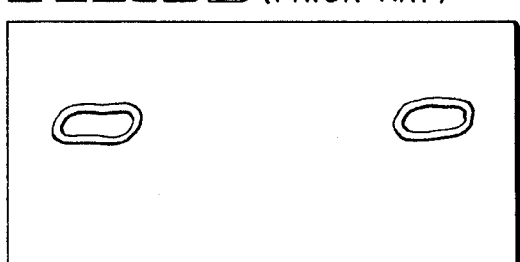
Figure 5F:
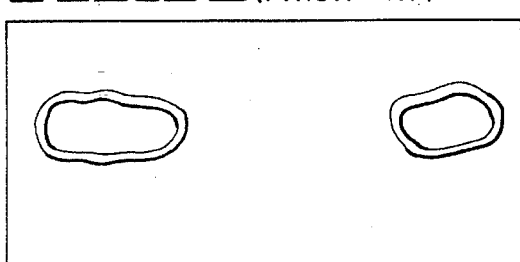

Once the second program has been executed, the examining physician can retrieve each reconstructed cross-sectional image individually from memory for display on the video monitor and if desired, for taking a photograph thereof. To do this, the physician displays the three-dimensional model of the colon on the monitor, positions the cursor adjacent the selected colon segment, as shown in FIG. 3, and then uses the keyboard to input the appropriate display instruction to the computer, whereby the selected reconstructed cross-sectional image is displayed on the same monitor and replaces the view of the three-dimensional model. The user can return to the view of the three-dimensional model by inputting the appropriate instructions to the computer. The method of the present invention may also include the capability for displaying the three-dimensional model with cursor on one monitor, while displaying the retrieved reconstructed cross-sectional images on another monitor. In addition, the program preferably allows the physician to view the reconstructed cross-sectional images in the consecutive sequential order of the sections along the length of the colon, generally in the manner of flipping through the pages of a book. It will be appreciated that the reconstructed images produced by the present invention provide a visualization of the colon as if it were a tube that had been straightened out and viewed from either end by multiple, consecutive contiguous thin axial sections. This is because each reconstructed cross-sectional image is correctly angled in perpendicular relation to the longitudinal axis of the colon lumen. Using the method of the present invention to examine a colon, a physician will be able to readily detect polyps and tumors as small as 2 millimeters which intrude into the lumen of each cross-sectional image and which provide anatomic evidence of an abnormality in the colon. As shown in FIG. 4, a polyp which intrudes into the colon lumen will be viewed as a roughly perpendicular protrusion to the internal colon wall and will show more precisely its true pathologic relation to the colon wall than would be shown by prior art images of the colon produced by CT scanning because such images are oblique and distorted. The reconstructed cross-sectional images produced by the present invention can therefore assist the physician in determining the gross pathologic significance of a polyp or tumor.

Since many modifications, variations and changes in detail can be made to the described preferred embodiment of the invention, it is intended that all matters in the foregoing description and shown in the accompanying drawings be interpreted as illustrative and not in a limiting sense. For example, it will be appreciated that the method of this invention may be carried out on other viscous tissues within a body, such as arteries. Thus, the scope of the invention should be determined by the appended claims and their legal equivalents.

What is claimed is:

1. A method of imaging a colon to obtain a desired cross-sectional image of at least one substantially thin segment of the colon, which image is generally perpendicular to the longitudinal axis of the colon lumen, comprising the steps of:

(a) inflating the colon with gas;

(b) scanning the abdominal region by using scanner means to obtain initial sets of data representing a plurality of first cross-sectional images of the entire colon taken along the longitudinal axis of the abdomen;

(c) storing said initial sets of data in a memory;

(d) processing said initial sets of data to reconstruct a three-dimensional image of the colon;

(e) storing data representing said three-dimensional image in said memory;

(f) displaying said three-dimensional image on a display;

(g) using input means to select at least one substantially thin segment of said displayed three-dimensional image;

(h) processing said initial sets of data and said three-dimensional image data to calculate a reconstructed cross-sectional image for said at least one segment that is disposed in perpendicular relation to the longitudinal axis of the colon lumen; and (i) storing data representing said reconstructed cross-sectional image in memory.

2. A method as recited in claim 1 wherein reconstructed cross-sectional images are calculated for additional contiguous substantially thin segments along the length of the entire colon.

3. A method as recited in claim 2 wherein said processing step of said initial data and said three dimensional image data uses the parameters of smallest cross-sectional diameter, area and circumference as applied to said segments to calculate said reconstructed cross-sectional images.

4. A method as recited in claim 3 further comprising the steps of retrieving said data representing said reconstructed cross-sectional images from memory and displaying said reconstructed cross-sectional images on said display.

5. A method as recited in claim 3 wherein said selecting step comprises selecting segments each having a thickness in the range of 1–10 millimeters.

6. A method as recited in claim 1 wherein said scanning step is carried out with a computed tomographic scanner.

7. A method as recited in claim 1 wherein said scanning step is carried out with a magnetic resonance imaging apparatus.

8. A method as recited in claim 1 wherein said inflating step is carried out utilizing a pump apparatus having an enema tip which is inserted into the rectum.

9. A method as recited in claim 1 wherein said inflating step is carried out utilizing a gas selected from the group consisting of ambient air, carbon dioxide, nitrous oxide and xenon.

10. A method as recited in claim 4 further comprising the step of displaying said cross-sectional images on a display in a sequential order corresponding to the sequence of said segments along the length of said colon.

11. A method as recited in claim 1 wherein said processing step of said initial data comprises processing said initial sets of data to reconstruct a three-dimensional model of the gas-filled lumen of the colon.

12. A method of imaging a viscous tubular structure within a body to obtain a desired cross-sectional image of at least one substantially thin segment of said viscous tubular structure, which image is generally perpendicular to the longitudinal axis of the lumen of said viscous tubular structure, comprising the steps of:

(a) inflating said viscous tubular structure;

(b) scanning the body region wherein said viscous tubular structure is located by using scanner means to obtain initial sets of data representing a plurality of first cross-sectional images of said viscous tubular structure taken along the longitudinal axis of the bodily region;

(c) storing said initial sets of data in a memory;

(d) processing said initial sets of data to reconstruct a three-dimensional image of said viscous tubular structure;

(e) storing data representing said three-dimensional image in said memory;

(f) displaying said three-dimensional image on a display;

(g) using input means to select at least one substantially thin segment of said displayed three-dimensional image;

(h) processing said initial sets of data and said three-dimensional image data to calculate a reconstructed cross-sectional image for said at least one segment that is disposed in perpendicular relation to the longitudinal axis of the lumen of said viscous tubular structure; and (i) storing data representing said reconstructed cross-sectional image in memory.

* * * * *

Adverse Decisions In Interference

Patent No. 5,458,111, Carl G. Coin, COMPUTED TOMOGRAPHIC COLONOSCOPY, Interference No. 104,366, final judgment adverse to the patentee rendered August 30, 2000, as to claims 1-12.
*(Official Gazette October 17, 2000)*